US008674323B2

(12) United States Patent
Schampers et al.

(10) Patent No.: US 8,674,323 B2
(45) Date of Patent: Mar. 18, 2014

(54) FORMING AN ELECTRON MICROSCOPE SAMPLE FROM HIGH-PRESSURE FROZEN MATERIAL

(71) Applicant: FEI Company, Hillsboro, OR (US)

(72) Inventors: Rudolf Johannes Peter Gerardus Schampers, Tegelen (NL); Michael Frederick Hayles, Eindhoven (NL); Dirk Arie Mattheus de Winter, Utrecht (NL); Christianus Thomas Wilhelmus Maria Schneijdenberg, Utrecht (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 13/934,925

(22) Filed: Jul. 3, 2013

(65) Prior Publication Data

US 2014/0014834 A1 Jan. 16, 2014

Related U.S. Application Data

(60) Provisional application No. 61/671,222, filed on Jul. 13, 2012.

(30) Foreign Application Priority Data

Jul. 13, 2012 (EP) .................................. 12176254

(51) Int. Cl.
*H01J 37/20* (2006.01)
*H01J 37/26* (2006.01)
(52) U.S. Cl.
USPC ....... 250/440.11; 250/307; 250/310; 250/311
(58) Field of Classification Search
USPC ............ 250/306, 307, 309, 310, 311, 440.11, 250/441.11, 442.11, 443.1
See application file for complete search history.

(56) References Cited

U.S. PATENT DOCUMENTS

| 7,767,979 | B2 | 8/2010 | Dona |
| 8,011,259 | B2 | 9/2011 | Dona |
| D657,474 | S | 4/2012 | Dona |
| 2003/0127776 | A1 * | 7/2003 | Carlson et al. ................. 264/406 |
| 2013/0205808 | A1 * | 8/2013 | Mulders et al. .................... 62/62 |

FOREIGN PATENT DOCUMENTS

| EP | 2009421 | 12/2008 |
| EP | 2009421 A1 * | 1/2009 ............... G01N 1/06 |

OTHER PUBLICATIONS

Al-Amoudi, A., et al., 'An oscillating cryo-knife reduces cutting-induced deformation of vitreous ultrathin sections,' Journal of Microscopy, Oct. 1, 2003, pp. 26-33, vol. 212.

(Continued)

*Primary Examiner* — Nicole Ippolito
(74) *Attorney, Agent, or Firm* — Scheinberg & Associates, PC; Michael O. Scheinberg

(57) ABSTRACT

A method of forming a sample from a capillary with high-pressure frozen sample material comprises providing a high-pressure capillary with vitrified sample material at a temperature $T_1$ below the glass transition temperature $T_g$, cutting the capillary, warming the capillary to a temperature $T_2$ between temperature $T_1$ and temperature $T_g$, cooling the capillary to a temperature $T_3$ below temperature $T_2$, as a result of which material is extruded from the capillary, and freeing a sample from the extruded sample material at a temperature below temperature $T_g$. Repeating this temperature cycle results in further extrusion of the sample material. The extruded material can then be sliced by, for example, ion beam milling.

17 Claims, 2 Drawing Sheets

(56) References Cited

OTHER PUBLICATIONS

Hayles, Michael F., et al., 'The making of frozen-hydrated, vitreous lamellas from cells for cryo-electron microscopy,' Journal of Structural Biology, Jul. 16, 2010, pp. 180-190, vol. 172.

Karreman, Matthia, et al., 'VIS2FIX: A High-Speed Fixation Method for Immuno-Electron Microscopy,' Traffic, 2011, pp. 806-814, vol. 12.

'Leica EM PACT2: High Pressure Freezer,' retrieved Jul. 3, 2013, 12 pgs.

* cited by examiner

FORMING AN ELECTRON MICROSCOPE SAMPLE FROM HIGH-PRESSURE FROZEN MATERIAL

The present application claims priority from U.S. Prov. App. No. 61/671,222, filed Jul. 13, 2012, which is hereby incorporated by reference.

The invention relates to a method of forming a sample from a capillary with high-pressure frozen sample material, the method comprising:

A step of providing a high-pressure capillary with vitrified sample material at a temperature $T_1$ below the glass transition temperature $T_g$, and A step of cutting the capillary.

Such a method is known from "Leica EM PACT application brochure" from Leica Microsystems, available on the internet, further referred to as the Leica brochure [-1-].

When observing a sample in a TEM, the sample is irradiated with a beam of electrons with an energy of typically between 60 keV and 300 keV, although lower and higher energies are known to be used. The image is formed by observing electrons transmitted through the sample. Therefore the sample must be a thin sample, with a thickness of typically less than 1 µm, more specifically less than 200 nm, and most specifically less than 100 nm. When observing biological samples the samples is typically sliced in thin slices. To that end the samples are first solidified. This is done by e.g. replacing all water with a plastic in so-called resin embedding, but superior results are achieved by cryo-imaging.

Cryo-imaging involves the freezing of the sample material to a cryogenic temperature without forming ice crystal (as these damage the sample), slice the sample at the cryogenic temperature, and inspect the sample at the cryogenic temperature.

Transmission Electron Microscopes capable of observing the sample at cryogenic temperature are commercially available.

Also apparatuses for freezing the sample are commercially available. Part of these apparatuses use the principle of high-pressure freezing, in which the sample, contained in a holder, is first pressurized to a pressure of approximately 2100 bar, and then rapidly cooled to a temperature $T_g$ of approximately 165 K, the glass transition temperature of water. The container is then depressurized and the sample material inside the container can then be freed.

In one group of such apparatuses capillaries, such as copper capillaries, are used. An example of such a apparatus and method of sample preparation using these capillaries is described in the Leica brochure [-1-], more specifically pages 7 and 8. Sample material is sucked in a capillary of copper with an outer diameter of 650 µm and an inner diameter of 300 µm. this capillary is then enclosed in a holder, exposed to a pressure of 2100 bar and then cooled rapidly (typically >600 K/s) to a temperature of 165 K or less.

The prior art method proceeds by immersing the holder with the capillary and sample material in liquid nitrogen ($LN_2$), removing the capillary from the holder, and transferring the capillary to a cryoultramicrotome. In the cryoultramicrotome the material of the capillary is removed and the sample material is sectioned to form samples.

It is noted that it is also known to section sample material at cryogenic temperatures, followed by a step of freeze-substitution and a step of immunolabeling at room temperature, followed by inspection at room temperature. See M. Karreman et al., "VIS2FIX: A High-Speed Fixation Method for Immuno-Electron Microscopy", Traffic, Vol 12, issue July 2011, pages 806-814, further referred to as Karreman [-2-].

It is known that mechanical sectioning of samples introduces artifacts, see for example "An oscillating cryo-knife reduces cutting-induced deformation of vitreous ultrathin sections", A. Al-Amoudi et al., J. Microsc. 2003 (Oct), 212(Pt 1), pages 26-33, further referred to as Al-Amoudi [-3-]. These artifacts result from the mechanical forces on the sample material. Therefore lately Focused Ion Beam (FIB) machining is used for sectioning sample material, in which material is milled (sputtered away) with a focused ion beam, for example a Gallium ion beam with an energy of between 10 and 40 keV. FIB sectioning enables forceless cutting.

A disadvantage of FIB sectioning of a capillary is that the copper or steel of the capillary has a low milling rate compared to biological material. Also, the wall thickness is, compared to the diameter of the core of sample material, rather large. This implies that a large amount of capillary material must be removed at a low milling rate to form a slice of sample material (a sample, also known as a lamella). The low milling rate and the relatively large amount of material result in long throughput times.

There is a need for forming samples from capillaries without exerting force on the sample material and with a higher throughput time than prior art methods.

The invention intends to provide a solution to that.

To that end the method according to the invention is characterized by a step of warming the capillary to a temperature $T_2$ between $T_1$ and $T_g$, a subsequent step of cooling the capillary to a temperature $T_3$ below $T_2$, as a result of which material is extruded from the capillary, and a step of freeing a sample from the extruded sample material at a temperature below $T_g$.

Inventors found surprisingly that by raising the temperature of the capillary and then cooling it again resulted in an extrusion of sample material from the open end of the capillary. Inventors are unable to provide a physical explanation for this. It is not solely the result of thermal expansion, as the extrusion is observed at the same temperature where originally the capillary was cut.

It is noted that extrusion of ice due to a lowering of temperature is known from EP patent application publication EP2009421A1, specifically paragraph [0047]. However, this application mentions extrusion due to the lowering of the temperature during the freezing, and does not disclose or indicate that this is due to rising and subsequent lowering of the temperature after freezing.

In an embodiment of the invention the subsequent step of cooling the capillary to a temperature $T_3$ below temperature $T_2$ comprises immersing the capillary in a liquid with a temperature below temperature $T_2$, specifically immersing in liquid ethane, liquid propane or liquid nitrogen.

Cooling of the capillary is easiest by plunging it in, for example liquid ethane, propane or nitrogen.

It is noted that before mentioned patent application publication EP2009421A1 implies that the temperature is increased while introducing the sample in a transmission electron microscope (TEM), but introducing a sample in a TEM implies that no subsequent immersion in a liquid can take place, as the innards of a TEM are a high vacuum.

In a preferred embodiment the capillary is a metal capillary.

Although capillaries of cellulose are known, the extrusion is only observed with metal capillaries. Such capillaries are preferably made of a metal comprising iron or copper, iron and/or aluminum.

In another preferred embodiment the difference between temperature $T_2$ and $T_3$ is more than 20 K, preferably more than 50 K.

The effect is believed to be caused by thermal expansion/contraction. Assuming a constant linear thermal expansion coefficient for capillary and core material, the length of the extruded core material is proportional to the temperature difference. A higher temperature difference thus results in a larger protrusion.

In an embodiment the step of freeing a sample comprises cutting with a focused ion beam.

Cutting a slice of material, such as ice with biological material, is a method known per se to the skilled artisan.

In a further embodiment the freed sample is a lamella.

A lamella, that is a approximately rectangular slice of sample material with a thickness of between 30 and 300 nm, is a preferred sample in transmission electron microscopy.

In still a further embodiment the method further comprises a step of inspection in an electron microscope.

Forming the sample should lead to a sample to be inspected in a TEM or STEM. The inspection can be performed at cryogenic temperatures, or at room temperature after, for example, freeze substitution and immune-labeling the sample at room temperature. Such a method is known from Karreman [-2-]

In a preferred embodiment the step of warming the capillary to a temperature $T_2$ between temperature $T_1$ and temperature $T_g$ and the subsequent step of cooling the capillary to a temperature $T_3$ below temperature $T_2$, as a result of which material is extruded from the capillary is followed by a further step of warming the capillary to a temperature $T_2$ between temperature $T_1$ and temperature $T_g$ and a further subsequent step of cooling the capillary to a temperature $T_3$ below temperature $T_2$, as a result of which more material is extruded from the capillary.

Inventors found surprisingly that in many cases a repetition of the warming/cooling cycle resulted in a further extrusion of sample material, although the process could not be repeated indefinitely.

BRIEF DESCRIPTION OF THE DRAWINGS

The invention is now elucidated using figures, in which identical reference numerals refer to corresponding features.

To that end:

FIG. 1 schematically shows a flowchart of the method according to the invention.

Figure 1:
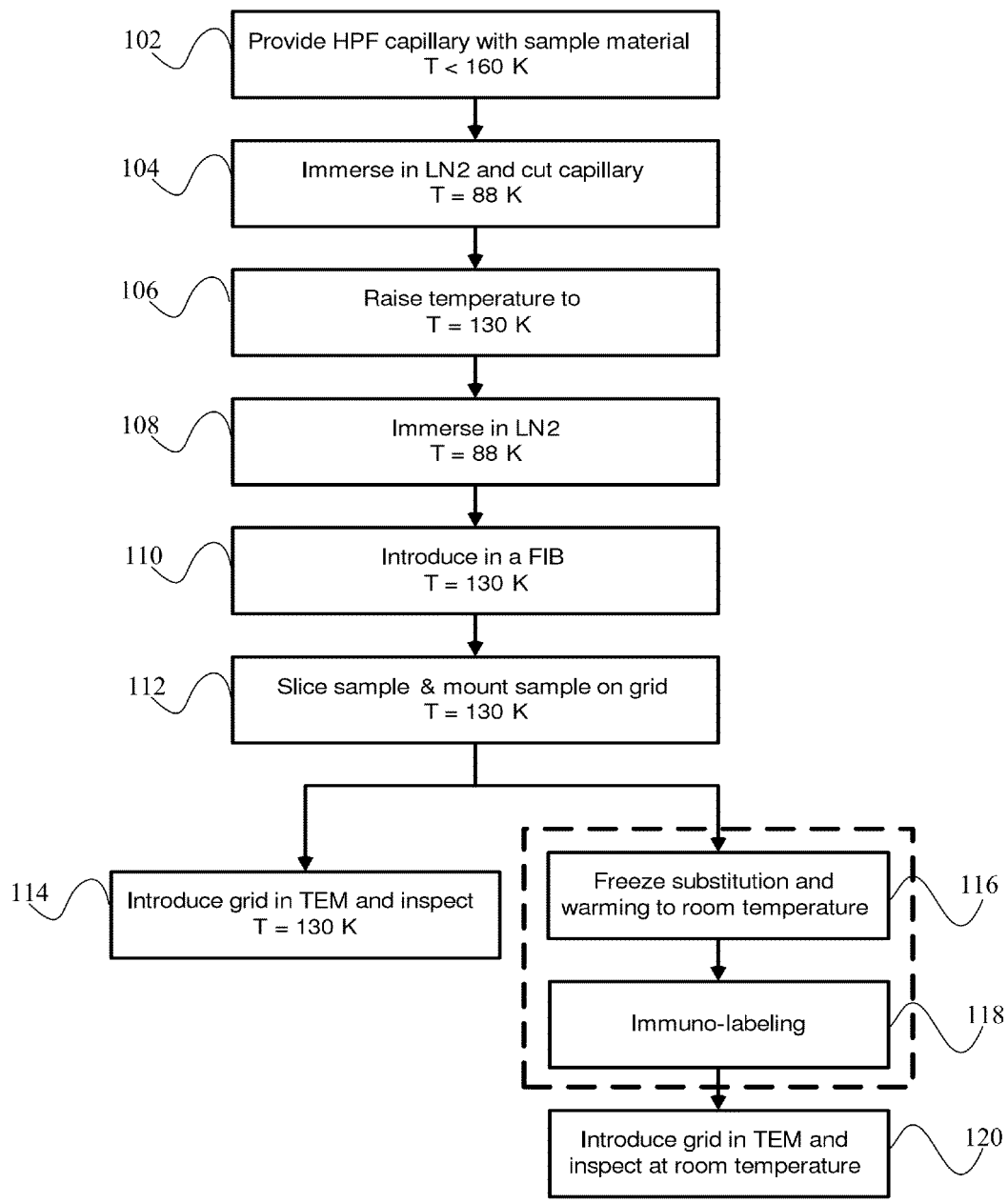
FIG. 1 schematically shows a flow-chart of the method according to the invention.

In step 102 a capillary with high pressure frozen sample material is provided in $LN_2$. Such a capillary, for example a copper capillary, can be prepared by a high pressure freezer, such as an EM PACT2™ from Leica Microsystems Gmbh., Wetzlar, Germany.

In step 104 the capillary, immersed in $LN_2$, is introduced in a cryo-ultramicrotome to cut the capillary, such as a EM-UC7/FC7™ from Leica Microsystems Gmbh., Wetzlar, Germany. This cutting is routinely done while the capillary is submerged in $LN_2$.

In step 106 the cut capillary is 'heated' to a temperature of approximately 130 K, some 50 K above the temperature of (boiling) $LN_2$ (77 K).

In step 108 the cut capillary is cooled to $LN_2$ temperature again by immersing it in $LN_2$.

In step 110 the truncated capillary is introduced in a FIB or Dual-Beam apparatus at a temperature of 130 K. A suited Dual-Beam apparatus, comprising a Focused Ion Beam column for milling and a Scanning Electron Microscope column for imaging, is, for example, the Quanta 3D™ from FEI Company, Hillsboro, USA. Inventors observed that in most cases (approximately 90% of the cases) sample material was extruded from the capillary.

In step 112 a sample is formed from the core of sample material and mounted on a sample carrier.

The protruding core can now be sectioned with the ion beam at a cryogenic temperature. This is a method known per se to the skilled person. If necessary the sample can not only be sectioned with an ion beam, but also thinned. The completed sample is then deposited on a sample carrier. Such a sample carrier is preferably a TEM grid (typically 3 mm round) or another sample carrier dedicated for use in a TEM, such as the sample carrier described in U.S. Pat. No. 7,767,979.

In step 114 the sample, mounted on the sample carrier, is introduced and inspected/observed in an electron microscope, such as a Transmission Electron Microscope (TEM) or a Scanning Transmission Electron Microscope (STEM).

It is noted that this inspection may be an inspection at a cryogenic temperature in a cryo-TEM, such as the Titan Krios™ from FEI Company, Hillsboro, USA, or in a room temperature TEM, such as the Titan 80-300™ from FEI Company, Hillsboro, USA.

Alternatively, instead of step 114 a step 116 of freeze substitution and warming of the sample to room, followed by a step 118 of immuno-labeling at room temperature can be performed. In this way a correlative light/electron microscope may be used, observing with fluorescent labels for navigation and making images with electron optical resolutions of less than 1 nm.

This method is described in Karreman [-2-] as the VIS2FIX$_{FS}$ method. Another method resulting in a sample at room temperature, the VIS2FIX$_H$ method, is also disclosed in Karreman [-2-].

Using this method, resulting in a sample at room temperature, the imaging can take place at room temperature as well in step 120.

It will be clear to the person skilled in the art that this sequence of steps is one of many: optionally the warming/cooling cycles of steps 106/108 can be repeated. The temperatures can be chosen different within limits by using for example propane instead of liquid nitrogen, etc. Also staining/labeling steps for electron microscopy (for example with electron dense materials as uranyl, osmium tetroxide, quantum dots, heavy metal clusters, etc.) can be introduced. Further it is explicitly noted that the temperatures mentioned are should not be interpreted as absolute limits: what is important is that the sample material does not change from its amorphous or glassy state to a crystalline state (by keeping the temperature below the glass transition temperature $T_g$), and that a large temperature difference between steps 104, 106 and 108 ($T_1$ and $T_2$) causes a larger extrusion than a small temperature difference.

Figure 2:
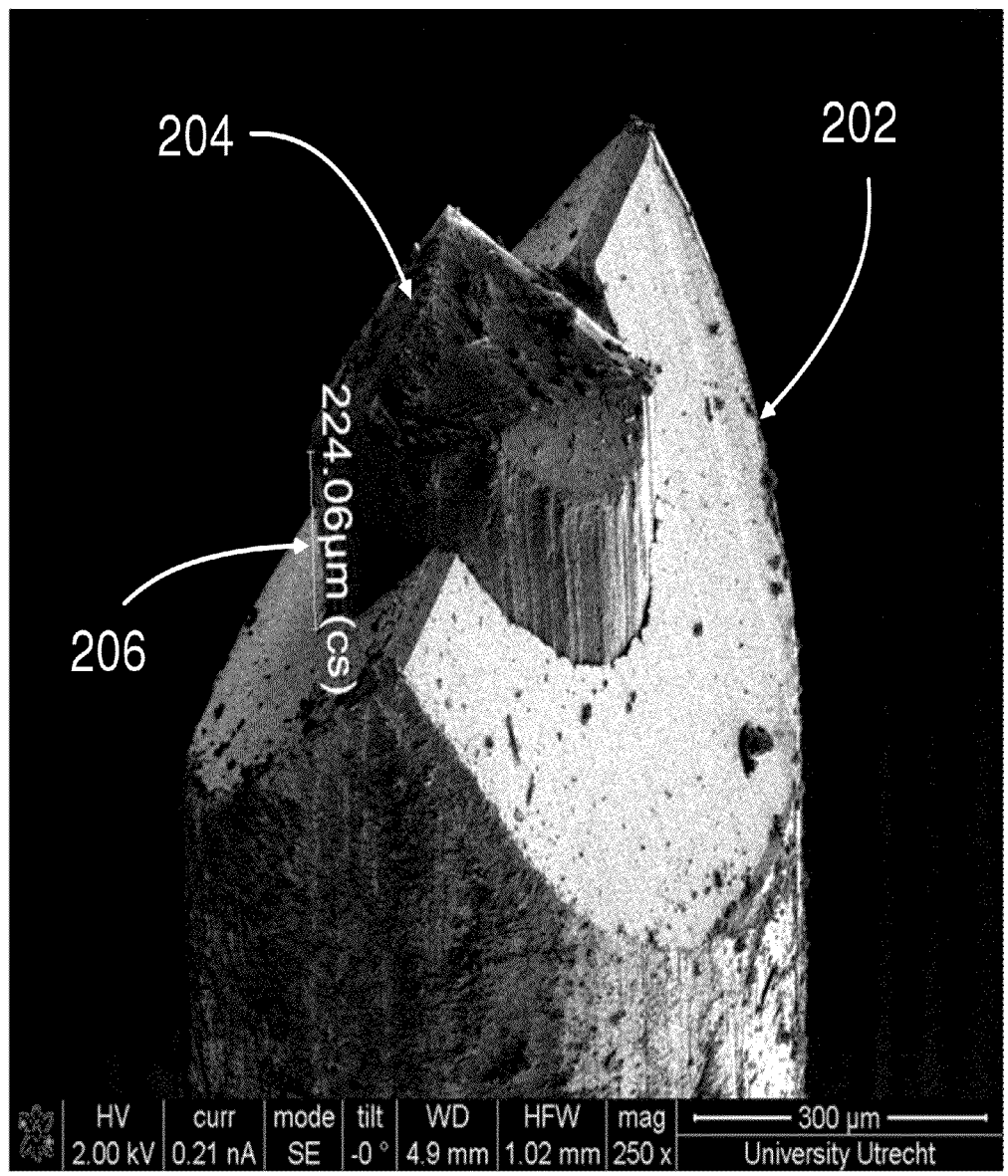
FIG. 2 shows a photo of a capillary with extruded sample material.

FIG. 2 shows a picture taken with a SEM, showing a capillary with sample material. The capillary 202 is a copper capillary with an external diameter of approximately 650 µm and an internal diameter of 300 µm. The extruded core 204 is vitreous ice with biological material in it, the biological material comprising for example cells, bacteria, viruses, etc., that extends over a length 206 of 224 µm It is mentioned that in electron microscopy "biological material" often refers to material that contains mainly hydrocarbons, and thus includes polymers, plastics, etc. The reason for this is that all these materials show weak contrast in an electron microscope as most of the nuclei are light nuclei, the nuclei showing comparable interaction with the electrons that irradiate the sample. Therefore in this context all material containing mainly hydrocarbons is included in the phrase "biological material".

NON-PATENT LITERATURE

[-1-] "Leica EM PACT application brochure", http://www.leica-microsystems.co.kr/pdfs.nsf/(ALLIDs)/D5AA3952E2A44A56C1256F100000B5CC/$FILE/EM_PACT_Application_Brochure_09_04.pdf

[-2-] "VIS2FIX: A High-Speed Fixation Method for Immuno-Electron Microscopy", M. Karreman et al., Traffic, Vol 12, issue July 2011, pages 806-814.

[-3-] "An oscillating cryo-knife reduces cutting-induced deformation of vitreous ultrathin sections", A. Al-Amoudi et al., Journal of Microscopy, Vol. 212 Issue 1, Pages 26-33.

We claim as follows:

1. Method of forming a sample from a capillary with high-pressure frozen sample material, the method comprising:
   providing a high-pressure capillary with vitrified sample material at a temperature $T_1$ below the glass transition temperature $T_g$,
   cutting the capillary,
   warming the capillary to a temperature $T_2$ between temperature $T_1$ and temperature $T_g$,
   cooling the capillary to a temperature $T_3$ below temperature $T_2$, as a result of which material is extruded from the capillary, and
   freeing a sample from the extruded sample material at a temperature below temperature $T_g$.

2. The method of claim 1 in which cooling the capillary to a temperature $T_3$ below temperature $T_2$ comprises immersing the capillary in a liquid with a temperature below temperature $T_2$.

3. The method of claim 2 in which the liquid comprises liquid ethane, liquid propane or liquid nitrogen.

4. The method of claim 1 in which the capillary is a metal capillary.

5. The method of claim 4 in which the metal comprises copper and/or iron and/or aluminium.

6. The method of claim 1 in which the difference between temperature $T_2$ and $T_3$ is more than 20 K.

7. The method of claim 1 in which freeing a sample comprises cutting with a focused ion beam.

8. The method of claim 1 in which the freed sample is a lamella.

9. The method of claim 8 in which the method further comprises inspection of the freed sample in an electron microscope.

10. The method of claim 9 in which the electron microscope comprises a transmission electron microscope (TEM), a scanning transmission electron microscope (STEM), or a cryo-TEM.

11. The method of claim 8 in which the lamella has a thickness between 30 nm and 300 nm.

12. The method of claim 1 in which warming the capillary to a temperature $T_2$ between temperature $T_1$ and temperature $T_g$ and cooling the capillary to a temperature $T_3$ below temperature $T_2$, as a result of which material is extruded from the capillary is followed by warming the capillary to a temperature $T_2$ between temperature $T_1$ and temperature $T_g$ and cooling the capillary to a temperature $T_3$ below temperature $T_2$, as a result of which more material is extruded from the capillary.

13. The method of claim 1 in which the difference between temperature $T_2$ and $T_3$ is more than 50 K.

14. The method of claim 1 in which the freed sample has a thickness less than 1 μm.

15. The method of claim 1 in which the freed sample has a thickness less than 100 nm.

16. The method of claim 1 in which the freed sample has a thickness less than 200 nm.

17. The method of claim 1 in which cutting the capillary is performed using a cryo-ultramicrotome.

* * * * *